United States Patent
Kondakov et al.

(10) Patent No.: US 10,898,447 B2
(45) Date of Patent: Jan. 26, 2021

(54) FINISHED PHARMACEUTICAL FORM WITH INDIVIDUAL MEDICINE DOSING CAPABILITY (EMBODIMENTS) AND METHODS OF ITS PRODUCTION AND USE

(71) Applicant: PharmPrint LLC, Moscow (RU)

(72) Inventors: Sergey Emilevich Kondakov, Moscow (RU); Aleksandr Pavlovich Osipov, Moscow (RU); Mikhail Yakovlevich Melnikov, Moscow (RU); Dmitry Mikhailovich Mikhailov, Moscow (RU); Maxim Yurievich Mitrohin, Moscow (RU); Sergey Olegovich Belezkii, Moscow (RU); Vladimir Vladimirovich Gordeev, Moscow (RU)

(73) Assignee: Psirrros Inc., New Canaan, CT (US)

( * ) Notice: Subject to any disclaimer, the term of this patent is extended or adjusted under 35 U.S.C. 154(b) by 0 days.

(21) Appl. No.: 16/345,448

(22) PCT Filed: Jul. 3, 2017

(86) PCT No.: PCT/RU2017/000482
§ 371 (c)(1),
(2) Date: Apr. 26, 2019

(87) PCT Pub. No.: WO2018/080337
PCT Pub. Date: May 3, 2018

(65) Prior Publication Data
US 2019/0247319 A1    Aug. 15, 2019

(30) Foreign Application Priority Data

Oct. 27, 2016 (RU) ................................ 2016142022
Feb. 27, 2017 (RU) ................................ 2017106044

(51) Int. Cl.
*A61K 9/70* (2006.01)
*A61K 9/00* (2006.01)
*A61K 47/38* (2006.01)

(52) U.S. Cl.
CPC .......... *A61K 9/7007* (2013.01); *A61K 9/0056* (2013.01); *A61K 9/0095* (2013.01); *A61K 47/38* (2013.01)

(58) Field of Classification Search
CPC .... A61K 9/0092; A61K 9/7015; A61K 31/00; A61K 9/00
See application file for complete search history.

(56) References Cited

U.S. PATENT DOCUMENTS 2,928,538 A    3/1960 Mills
4,712,460 A    12/1987 Allen et al.
4,925,670 A    5/1990 Schmidt
2005/0233000 A1    10/2005 Figueroa et al.
2012/0225100 A1*   9/2012 Darcy .................. A61K 9/0056 424/400
2013/0006220 A1*   1/2013 Yribarren .......... A61M 25/0119 604/509
2016/0101108 A1    4/2016 Sandler et al.

FOREIGN PATENT DOCUMENTS

| RU | 2010111356 A | 5/2012 |
|---|---|---|
| RU | 2519670 C2 | 6/2014 |
| RU | 2674692 C2 | 12/2018 |
| WO | 2012/040262 A1 | 3/2012 |
| WO | 2014/039378 A1 | 3/2014 |
| WO | 2014147377 A1 | 9/2014 |
| WO | 2014/188079 A1 | 11/2014 |

OTHER PUBLICATIONS

El-Darawy et al (Forensic Science, 1974, vol. 4, pp. 171-176, abstract) (Year: 1974).*
Genina et al (European Journal of Pharmaceutical Sciences, 2012, vol. 47, pp. 615-623) (Year: 2012).*
Voura et al (Pharmaceutical Technology Europe, 2011, pp. 32-36) (Year: 2011).*
International Search Report and Written Opinion of PCT/RU2017/000482, dated Nov. 30, 2017.
http://www.pharmspravka.ru/farmatsevticheskie-vorosyi-i-otvetyi/chto/chto-takoe-filtr-paket.html, 2015, pdf 2 pages.
English Abstract of RU2521395 (equivalent of RU2010111356) retrieved on Espacenet on Apr. 18, 2019.
Genina et al., "Tailoring controlled-release oral dosage forms by combining inkjet and flexographic printing . techniques", European Journal of Pharmaceutical Sciences, 2012, vol. 47, pp. 615-923.
Sandler, "Inkjet printing of drug substances and use of porous substrates-towards individualized dosing", Journal of Pharmaceutical Sciences, 2011, vol. 100, No. 8, pp. 3386-3395; https://www.ncbi.nlm.nih.gov/pubmed/21360709-translation of abstract.
Voura et al., "Printable medicines: A microdosing device for producing personalised medicines", Pharmaceutical Technology Europe, 2011, vol. 23, Issue 1, 6 pages.
Lukin et al., "Cyclic Adsorption Processes. Theory and Calculation", Khimiya, Leningrad, 1989, pp. 89-90, ISBN 6-7245-0317-4.
Zhorov et al., Study and Calculation of Oxidation and Sorption Processes, Chechen-Ingush Publishing, Grozny, 1979, pp. 110-111—translation of above pages into English attached.

* cited by examiner

*Primary Examiner* — Mark V Stevens
(74) *Attorney, Agent, or Firm* — Buckley, Maschoff & Talwalkar LLC

(57) ABSTRACT

This invention relates to medical science and pharmaceutical technology. A new type of finished pharmaceutical form with individual medicine dosing capability is described comprising a storage container and a carrier on which the medicine is applied. Methods of production and use of the finished pharmaceutical form for individual medicine dosing are suggested.

18 Claims, No Drawings

FINISHED PHARMACEUTICAL FORM WITH INDIVIDUAL MEDICINE DOSING CAPABILITY (EMBODIMENTS) AND METHODS OF ITS PRODUCTION AND USE

This invention relates to medical science and pharmaceutical technology.

In accordance with the applicable definition, a pharmaceutical form is an artificially attained condition of a medicine or a herbal medical raw material that makes it suitable for administering and provides for the required therapeutical effect (Order of the Ministry of Health of the Russian Federation No. 82 as of 29 Feb. 2000, "Implementation of the Industrial Standard on the Quality Standards for Medicines. Basic Provisions"), or a condition of a medicine compliant with the methods of its introduction and administering and providing for the achievement of the required therapeutical effect (Federal Law of the Russian Federation No. 61-FZ as of Dec. 4, 2010 "Circulation of Medicines").

The following common classification is used for medicines: by pharmaceutical form, by aggregation form, by target and by method of administering.

By pharmaceutical form, medicines have the following classification:
 undosed (unseparated): collections, medicinal pencils, skin glue, infusions, apozema, potions, elixirs and syrups;
 dosed/undosed: powders, granules, ointments (including pastes, crèmes, gels and liniments), plasters, suspensions, emulsions, solutions, mixtures and aerosols (including sprays);
 dosed (separated): briquettes, capsules (including spansules and pellets), pills (including coated pills, glossettes and medicinal chewing gums), pellets, candies, pastilles, eye films, transdermal therapeutic systems, suppositories (including sticks, pessaries, and balls) and drops.

By aggregation form, medicines have the following classification:
 hard: collections, medicinal pencils, powders, granules, briquettes, capsules (including spansules and pellets), pills (including coated pills and glossettes), pellets, medicinal chewing gums, marmalade etc., candies, pastilles and eye films;
 soft: including pastes, crèmes, gels and liniments), suppositories (including sticks, pessaries, and balls) and plasters (including transdermal therapeutic systems);
 liquid: infusions, apozema, potions, elixirs, syrups (including drops), suspensions, emulsions and mixtures;
 gaseous: aerosols (including sprays);
 sold, soft or liquid: extractions including liquid extractions, thick extractions, dry extractions and dried thick extractions.

By target and method of administering, medicines have the following classification:
 local;
 general (systematic or resorptive);
 enteral;
 parenteral (including injection pharmaceutical forms, i.e. powders, suspensions, emulsions, solutions, orodispersive or sublingual pharmaceutical forms).

Thus, no description is provided for a finished pharmaceutical form comprising a storage container and a membrane carrier the latter being membraneous material with the active pharmaceutical substance being applied thereupon with capability of resuspending to the solution upon submersion.

One of the most important tasks of medical science and pharmacology in the field of antibiotic therapy is the choice of individual medicine dosage. In fact, a common practice in the field is currently a strategy implying individual calculation of adequate antibacterial medicine dosage based on a profound consideration of individual patient characteristics, e.g. weight, gender, renal function quality etc. with the use of specialized computer software.

Similar problems associated with the choice of individual medicine dosage are common to almost every field of medical science, including gynecology, cardiology, urology, anesthesiology etc., especially in intensive care departments.

Pharmacology experts nowadays increasingly tend to the opinion that in the nearest future pharmacological factories will have to master the production of medicines in new pharmaceutical forms as are suitable for new therapeutic strategies and individual dosage approach for this problem is becoming increasingly pressing, especially in intensive care departments and stationary healthcare facilities that do not have or are not permitted to have in-house compounding pharmacies or pharmacological departments.

Therefore the object of this invention is providing a finished pharmaceutical form allowing, in the course of its administering, for fast delivery of individual medicine dosage in the form of a peroral solution without the necessity of using any additional dosing devices or technical metering means, and furthermore providing a simple method of its production.

Known is (RU Patent 2519670, published 20 Jun. 2014) a pharmaceutical form having the form of edible soft chewing medicine.

Disadvantage of that technical solution is the limited application range of the respective pharmaceutical form, e.g. for cattle and poultry in agriculture, and furthermore this finished pharmaceutical form is not suitable for individual medicine dosing.

Known is (RU Patent 2501395, published 27 Jun. 2014) a pharmaceutical form, said form being an implant containing an active medicinal substance. The implant is made from a polymer material serving as a matrix in which the medicine is distributed. The implant may have any arbitrary shape, e.g., a rod, and is based on a biologically degradable polymer.

Disadvantage of that invention is the necessity of using complex process equipment for achieving a homogeneous distribution of the active medicinal substance in the copolymer and the impossibility of individual medicine dosing, because the active substance is released into the solution during a long time thus making it impossible to control its concentration at any specific time.

Known is (PCT/US2013/057466 Aug. 30, 2013) a method of producing a finished pharmaceutical form with the use of a known device, i.e. a printer. In accordance with the known method of producing a finished pharmaceutical form, a 3D printer is used for printing differently sized peroral pills thus providing for individual medicine dosing.

Disadvantage of that invention is the necessity of the initial provision of a composition containing the active substance of the medicine and the media substance, the latter having strictly predetermined characteristics, i.e. melting and solidification points, for its use in a 3D printer, this greatly reducing the potential application range.

The closest counterpart of the technical solution provided herein is (WO/2014/188079 Apr. 14, 2016) a method of producing finished personified pharmaceutical form with the use of a known device, i.e. a jet printer, wherein the finished peroral pharmaceutical form of vitamins, mineral additives and/or nicotinic acid is produced with the use of a jet printer allowing applying the solutions of vitamins and/or nicotinic acid on powders of mineral additives, further wherein individual dosage is provided by dosing the quantity of powder intended for peroral administration.

Disadvantages of that invention are the necessity of modifying the original design of a jet printer for achieving homogeneous application of the active substance on the powder, the necessity of using only powders that are allowed for peroral administration and the impossibility of obtaining individual powder dosage without applying additional dosing devices or technical metering means.

The technical task solved by this invention is to provide a finished pharmaceutical form allowing, in the course of its application, for fast delivery of individual medicine dosage in the form of a peroral solution without the necessity of applying any additional dosing devices or technical metering means, and providing a simple method of its production.

The technical result achieved by implementing this invention includes simplifying the technology of pharmaceutical production, broadening the range of applicable medicines and providing the possibility of producing finished pharmaceutical forms having novel consumer properties.

It is suggested to achieve the abovementioned technical result by using the technical solution provided herein.

The technical solution provided herein characterizes the first embodiment of the finished pharmaceutical form for individual medicine dosing in accordance with this invention, the latter being in the form of a water-insoluble porous media wherein said porous media is selected such as to provide for the quantity desorption capability of the medicine applied onto said media using a jet printer.

The use of porous media is dictated by the aim to increase the area of the surface capable of adsorbing the medicine by increasing the total surface area of pores.

In some embodiments of this invention the surface of said porous media is provided such as to allow fragmentation. To this end the surface of said porous media is provided with marking lines that divide the surface of said membrane media into fragments, or the surface of said porous media is provided with perforations that divide the surface of said membrane media into fragments.

Preferably, said medicine is homogeneously applied onto the media.

Preferably, said porous media has a preset desorption coefficient for the medicine being applied onto it, in order to allow applying medicines onto membrane media taking into account water desorption losses.

Typically, the storage container and/or the porous media has marking to show the dose of the medicine desorbed from unit area of said media to the solution taking into account desorption losses.

Preferably, tape-shaped porous media are used, said media being wrapped onto a holder wherein said holder and the media wrapped around it are placed with the capability of rotation into the storage container, further wherein the distal end of said membrane media extends outside said container.

Furthermore, the technical solution provided herein characterizes the second embodiment of the finished pharmaceutical form for individual medicine dosing in accordance with this invention.

In accordance with the second embodiment of this invention, the finished pharmaceutical form is porous hydrophilic media containing the medicine immobilized in the membrane pores in a dry condition, obtained by preliminary introduction of a preset quantity of medicine into the pores of the media, followed by drying of the media, and capable of quantitative desorption to solution after porous media submersion into water. The pharmaceutical form provided herein contains medicine retained in the pores and possibly absorbed by the surface of the media, said medicine being capable of resuspending to the water phase, if necessary, as a result of the interaction of the porous media with water. The surface of the media can be hydrophilic due to the initial properties of the media material or due to its treatment with a hydrophilizing agent.

Along with immobilized medicine the surface of the porous media may further contain a coloring agent selected from coloring agents approved for use in the food industry. The color of the medicine and the coloring agent applied onto the surface of the media depend on the content of the medicine in order to allow color-based selection of the required medicine dosage.

In some embodiments of the technical solution provided herein the porous media with medicine and, possibly, coloring agent applied onto its surface allows fragmentation. This provides for the possibility of accommodating multiple medicine dosages on a single piece of said media. The fragmentation capability of said porous media can be provided by dividing the surface of said porous media with special separation marking lines that delimit the fragments the porous media surface is divided into. Said marking lines on the surface of said porous media with immobilized medicine and coloring agent can be in the form of perforations that divide porous media fragments.

In the preferred embodiment of the finished pharmaceutical form provided herein said medicine and coloring agent are homogeneously applied onto said porous media.

Said medicine and coloring agent can be applied onto said porous media by submerging said porous media into a solution containing the required concentrations of the medicine and the coloring agent. Alternatively, Said medicine and coloring agent can be applied onto said porous media by applying aliquot solutions of the medicine and the coloring agent on each of the individual fragments of the porous media using a jet printer, an automatic or a semiautomatic dosing device capable of operation with liquid pharmaceutical forms.

In the preferred embodiment of the invention said porous media has a pore size and a pore volume percentage allowing it to absorb and retain the required quantity of water solution within each individual fragment of porous media and, after drying, to quantitatively resuspend the dry active substance to the solution upon submersion of said fragment of porous media into water and subsequent exposure.

Typically, each medicine immobilized in the porous media is marked with an individual coloring agent having a specific color on the media and/or in water.

Different quantities of the same medicine immobilized in the porous media can be marked with individual coloring agents having specific colors on the media and/or in water. This will allow visually selecting the required quantity of medicine.

Said storage container and/or porous media show information on the dosage of medicine desorbed from each fragment of the porous media. The dose of medicine desorbed from each fragment of the porous media corresponds to a specific color or color intensity of the immobilized coloring agent.

In some embodiments of the invention said porous hydrophilic material can be water soluble. Said water soluble porous hydrophilic material can be selected, for example, from materials based on alginates or other natural polymers approved for use in the food or pharmaceutical industries.

In some embodiments of the invention said pharmaceutical form is capable, after drying, of reversibly and quantitatively resuspending the dry active substance and the fragment of the porous media to the solution upon submersion in water and subsequent exposure.

In some embodiments of the technical solution provided herein, thin porous media can be used, e.g. filtering membranes; although, relatively thick porous media can be used, e.g. unwoven pre-filters.

In some embodiments of the invention said porous media can be in the form of a narrow tape wrapped onto a rotating axial holder fastened in a container, the distal end of said tape extending outside said container to allow physical detachment of the delimited fragments. Sheet shaped media can be alternatively used.

In some embodiments of the finished pharmaceutical form provided herein, said finished pharmaceutical form additionally has marking made in a different color. Said marking may show auxiliary information, advertisement or other information.

Furthermore, the technical solution provided herein characterizes the method of producing the finished pharmaceutical form for individual medicine dosing.

In accordance with the method provided herein, the preliminarily prepared solution of the medicine is charged into the jet printer cartridges or into containers of any other automatic liquid media dosing device wherein the application of the medicine on the porous media is effected using said jet printer or other automatic liquid media dosing device, A further embodiment is available wherein said jet printer or other automatic liquid media dosing device is used for applying multiple active substances onto the porous media from different cartridges (containers).

The quantity of medicine applied onto said porous media can be controlled either by varying the concentration of the solution charged into jet printer cartridges, or by limiting the application time of solutions having the same concentration, or by software controlling the quantity of solution microdrops that are applied onto the unit surface area of the porous media.

Said porous media can be selected from materials based on cellulose or its modifications as well as paper or unwoven materials based on glass or polymer fibers or fibers produced from raw materials of vegetation origin (jutte, copra, leaf fiber, liana fiber, linen fiber etc.).

Furthermore, the technical solution provided herein characterizes the method of using the finished pharmaceutical form for individual medicine dosing.

In accordance with the method provided herein, the medicine containing porous media is removed from the container; one fragment of the porous media the area of which corresponds to the required quantity of the medicine is detached from the membrane media, the detached fragment is placed in a container with water or water solution, the container is shaken and the content is administered perorally in the form of a solution.

The technical solution provided herein may have different embodiments. Presented below are specific embodiments of the technical solution provided herein based on the use of a jet printer.

1. A finished pharmaceutical form for individual medicine dosing is produced on the basis of water-insoluble porous media, e.g. filtering paper Grade FM (slow filtration filtering paper, used for quantitative analysis as per the GOST 12026-76 USSR Standard).

A clean rechargeable jet printer cartridge is filled, through a disposable plastic syringe with an antibacterial filter for the removal of particles of greater than 45 micrometers in size, with the preliminarily prepared solution of the medicine having the required concentration.

The charged jet printer cartridge is installed in a jet printer. The filtering paper is loaded into the jet printer paper tray. The printer is connected to a personal computer. Using any software that allows printing monotone graphic images, printing is started with said charged cartridge preinstalled, the printing quality being preset to 150 dpi.

Preliminary experiments showed that the abovementioned printing quality setting provides for the quantity of printed dots per unit area that is sufficient, with account of desorption losses, for obtaining a quantity of medicine in 50 ml of water from 1 $cm^2$ of paper area that is equal to the average therapeutic dose for the specific medicine. After application the porous media is dried and packaged.

2. A finished pharmaceutical form for individual medicine dosing is produced on the basis of water-insoluble porous media, e.g. unwoven thermally bonded cloth Grade S2.04.063008.00 (used for the filtering of milk and other food, e.g. filtering cloth made by OAO Comitex). The cloth surface is divided into identical fragments with printed separation marking lines.

A clean rechargeable jet printer cartridge is charged, through a disposable plastic syringe with an antibacterial filter for the removal of particles of greater than 45 micrometers in size, with the preliminarily prepared solution of the medicine having the required concentration.

The charged jet printer cartridge is installed in a jet printer. The unwoven cloth is loaded into the jet printer paper tray. The printer is connected to a personal computer. Using any software that allows printing monotone graphic images, printing is started with said charged cartridge preinstalled, with the printing quality being preset to 300 dpi.

Preliminary experiments showed that the abovementioned printing quality setting provides for the quantity of printed dots per unit area that is sufficient, with account of desorption losses, for obtaining a quantity of medicine in 50 ml of water from 1 $cm^2$ of paper area that is equal to the average therapeutic dose for the specific medicine.

After application the porous media is dried and packaged.

In a similar manner pharmaceutical substances are applied onto unwoven composite materials that are typically used for the fabrication of filters and packaging materials (e.g. in sachet bags). These materials may contain any types of natural or semi synthetic fibers, e.g. 67% cotton fiber+33% polyester fiber, or 60% linen fiber (L+40% semi synthetic fiber, or 80% copra fiber+20% polyester fiber etc.

3. A finished pharmaceutical form for individual medicine dosing is produced on the basis of water-insoluble porous media, e.g. fiberglass filter Grade MGB (density 140 g/$m^2$ used for the filtration of water and protein solutions, e.g. fiberglass filter made by Sartorius, USA, or Munktel, Germany).

A clean rechargeable jet printer cartridge is filled, through a disposable plastic syringe with an antibacterial filter for the removal of particles of greater than 45 micrometers in size, with the preliminarily prepared solution of the medicine having the required concentration.

The charged jet printer cartridge is installed in a jet printer. The fiberglass material is loaded into the jet printer paper tray. The printer is connected to a personal computer.

Using any software that allows printing monotone graphic images, printing is started with said charged cartridge pre-installed, with the printing quality being preset to 250 dpi.

After application the material is dried in air.

4. A finished pharmaceutical form for individual medicine dosing is produced on the basis of water-insoluble porous media, e.g. filtering paper Grade FM (slow filtration filtering paper, used for quantitative analysis as per the GOST 12026-76 USSR Standard).

A clean uninterrupted ink supply system consisting of 4 identical containers is charged with preliminarily prepared solutions of medicines cleaned from dust and having the required concentrations.

The charged system is installed in a jet printer. The filtering paper with perforations preliminarily made on the surface for dividing its surface into fragments of similar size is loaded into the jet printer paper tray.

The printer is connected to a personal computer. Using any software that allows printing color graphic images, printing is started with said charged cartridges preinstalled, taking into account that color images are composed by software-generated superimposition of dots from different cartridges, with the printing quality being preset to 100 dpi for the black cartridge, 150 dpi for the cyan cartridge, 200 dpi for the magenta cartridge and 250 dpi for the yellow cartridge.

Preliminary experiments showed that the abovementioned printing quality setting provides for the quantity of printed dots per unit area that is sufficient, with account of desorption losses, for obtaining a quantity of medicine in 50 ml of water from 1 $cm^2$ of paper area that is equal to the respective dose. This provides for the method embodiment wherein a jet printer is used for applying multiple pharmaceutical substances from different cartridges onto porous media.

After application the porous media is dried in air.

5. Finished pharmaceutical form as described hereinabove in p. 2 is removed from the package, and differently sized portions are cut out from the cloth along the marking lines dividing the cloth into identical fragments such as to provide the required medicine concentrations for the first and the second fragments in 50 ml of water. The detached fragments are placed into a container with water, the container is shaken and its content is stirred to achieve a homogeneous distribution of the medicine in the solution; the insoluble media is removed from the water solution as necessary, and the solution is administered perorally in the form of a solution with the required concentration.

Presented below are specific examples of the embodiment of the technical solution provided herein.

The capabilities of the technical solution provided herein will be illustrated below with the example of a device, e.g. jet printer, the software of which allows applying water or water/organic solutions in one or multiple layers onto the predetermined areas of the porous media.

As noted above, this is not the sole possible embodiment of the technical solution provided herein. For example, combinations of a programmable dosing device or a programmable nozzle with a coordination table for the placement of porous media can be used.

Preliminarily calculations allowed determining the capacity of a 0.25 $cm^2$ unit area filtering paper fragment (pure cellulose, 1000±3 mg of medicine applied, 62±2 of medicine desorbed to 30 ml of potable water) to desorb applied acetylsalicylic acid to water. The calculations showed that to obtain a pharmaceutically optimum dose of 81 mg the user should apply 130 mg of 100% acetylsalicylic acid on the unit area of said media. As the solubility of acetylsalicylic acid in water/alcohol solutions of the abovementioned concentrations is close to 100%, 50 ml of a 10% acetylsalicylic acid solution was prepared. Using a jet printer with rechargeable cartridges the solution was applied on a 236.5 $cm^2$ specimen of media made from cellulose filtering material (size 21.5*11 $cm^2$, format Letter) with different printing qualities in dpi and different area filling densities. This format allows applying the active pharmaceutical substance on the entire media surface without taking into account the non-printable margins typically formed at the edges of an A4 format sheet. Following that the quantity of acetylsalicylic acid applied per unit area was analyzed depending on software controlled printing quality (in dpi). Using the specially plotted graduation curve the required printing densities in dpi were selected for applying 130 mg per 0.25 $cm^2$, or 520 mg/$cm^2$. The specimen was dried in a hot air flow for guaranteed removal of the water/alcohol solvent and packaged in a polymer container protecting the specimen from direct sunlight. Then the specimen was removed from the container and placed in a glass with water. After desorption of adsorbed acetylsalicylic acid to the water the medicine is ready for use.

A similar procedure was conducted for d, 1-2-(4-isobutylphenyl)-propionic acid (the active pharmaceutical substance of the Ibuprofen medicine) and a fiberglass membrane made by Algstrem, USA, used in immunology. The experiments showed that the possible quantity of d, 1-2-(4-isobutylphenyl)-propionic acid that can be applied on 1 $cm^2$ (unit area) of the abovementioned specimen is 300±2 mg, of which 246±2 was desorbed to 50 ml of potable water, i.e. 82%.

Taking into account that the typical dose of d, 1-2-(4-isobutylphenyl)-propionic acid in an Ibuprofen pill is 200 mg, the finished pharmaceutical form provided as above is capable of providing the typical dosage from unit area. For coloring the medicine solution, E162f (licopin) coloring agent was added to the solution which is approved for food industry in the Russian Federation and abroad (FDA/CFSAN Food Color Facts). After application and drying the finished pharmaceutical form had a reddish hue. The application and administration procedures for Ibuprofen are similar to the preparation and administration procedures for the abovementioned acetylsalicylic acid pharmaceutical form.

A similar procedure was conducted for Ampicillin antibiotic and water soluble alginate paper. A single Ampicillin dosage for adult administration is a 250-500 mg pill with an administration regimen of 3-4 times daily. For children with a body weight of below 20 kg the administration regimen is 12.5-25 mg/kg every 6 h. It has been determined that the quantity of the medicine that can be applied on 1 $cm^2$ (unit area specimen) at a time with a jet printer is 100 mg. Before application the medicine solution was colored with yellow coloring agent lutein (E161b). Simultaneously with the application of the active substance, technical notes and separation marking lines were printed from another cartridge in black (E153 coal food coloring). After application and drying the color of the finished pharmaceutical form was bright yellow with black marking and technical notes. The application and administration procedures for Ampicillin are similar to the preparation and administration procedures for the abovementioned acetylsalicylic acid pharmaceutical form.

Thus, without changing the preparation of the required finished pharmaceutical form a patient can separate an area of the media containing the required dosage of the antibiotic depending on the patient's weight and the doctor's order.

The above examples do not limit the applications of the finished pharmaceutical form provided herein.

One unconventional task that can be solved with the finished pharmaceutical form provided herein is local production of pharmaceutical forms taking into account potential applicable confessional aspects. Currently, questions arise in a number of Islamic states regarding the necessity of the Halal certification of pharmaceutical products because large international pharmaceutical companies often refuse to disclose the composition of auxiliary components they use for the production of finished pharmaceutical forms. The finished pharmaceutical form with individual medicine dosing capability provided herein can be produced locally in order to accommodate for any applicable requirements imposed upon pharmaceutical raw materials, components and their quality thus allowing for the establishment of pharmaceutical production facilities compliant with the Halal requirements.

One more potential application of this invention is the revival of compounding pharmacies so the doctor at the office can issue an electronic peroral pharmaceutical form order for a patient, such order to contain the name of the required pharmaceutical substance or preparation and the required dosage and administration regimen, following which the patient having paid for the order can receive the finished pharmaceutical form in accordance with this invention, containing printed administration regimen information and single dose fragment separation marking lines.

The above examples illustrate the feasibility of the technical result claimed herein in different embodiments of the technical solution provided herein.

What is claimed is a:

1. A finished pharmaceutical form comprising a plurality of individual water-soluble medicines of varied dosages, said form made up of water-insoluble porous media, wherein said porous media is adapted to provide for desorption of the water-soluble medicines upon placement in water or an aqueous solution, wherein the plurality of water-soluble medicines are retained in pores of the porous media and the water soluble medicines are applied to the porous media using a jet printer, and wherein each dosage of water-soluble medicine is separated from the other dosages of water-soluble medicine on the finished pharmaceutical form via separation marking lines on the porous media.

2. The finished pharmaceutical form of claim 1, wherein the surface of said porous media allows for fragmentation.

3. The finished pharmaceutical form of claim 1, wherein the surface of said porous media is provided with a marking for fragmenting the surface of said porous media.

4. The finished pharmaceutical form of claim 1, wherein the surface of said porous media is provided with perforations that divide the surface of said porous media into fragments.

5. The finished pharmaceutical form of claim 1, wherein each of the medicines are homogenously applied on their separate areas of the finished pharmaceutical form.

6. The finished pharmaceutical form of claim 1, wherein the porous media has a marking to show the dose of each water-soluble medicine that can be desorbed from a unit area of said media to the water or aqueous solution taking into account a desorption coefficient for each of said water-soluble medicines.

7. The finished pharmaceutical form of claim 1, wherein the porous media is tape-shaped, said media wrapped onto a holder, wherein said holder with the media has the capability of rotation into a storage container, and further wherein the distal end of said porous media extends outside said container.

8. A method of producing the finished pharmaceutical form of claim 1, wherein preliminarily prepared solutions of each of the water-soluble medicines are charged into jet printer cartridges and the application of the water-soluble medicines on the water-insoluble porous media is accomplished using a jet printer.

9. The method of claim 8, wherein said jet printer is used for applying multiple medicines onto the porous media from different cartridges.

10. The method of claim 8 wherein the quantity of the medicines applied onto said porous media is controlled by varying the concentration of the solution charged into the jet printer cartridges.

11. The method of claim 8, wherein the quantity of the medicines applied onto said porous media is controlled by limiting the application time of solutions having the same concentration.

12. The method of claim 8, wherein the quantity of each of the medicines applied onto said porous media is controlled by software controlling a quantity of microdrops of the solution that are applied onto a unit surface area of the porous media.

13. The method of claim 8, wherein said porous media is an unwoven material based on cellulose or modified cellulose.

14. The method of claim 8, wherein said porous media is paper.

15. The method of claim 8, wherein said porous media is an unwoven material based on natural fibers.

16. The method of claim 8, wherein said porous media is an unwoven material based on glass or polymer fiber.

17. A method of using the finished pharmaceutical form of claim 1, wherein the finished pharmaceutical form is removed from a container storing the finished pharmaceutical form; one fragment of the pharmaceutical form in the area of which corresponds to a required quantity of one or more of the water-soluble medicines is detached from said pharmaceutical form, the detached fragment is placed in another container with water or aqueous solution for desorption of the selected medicine or medicines into the water or the aqueous media, and the selected medicine or medicines are administered orally in the form of the solution produced after the desorption.

18. A storage container comprising the finished pharmaceutical form of claim 1, wherein the storage container includes markings to show the dose of each water-soluble medicine that can be desorbed from a unit area of said media to the water or aqueous solution taking into account a desorption coefficient for each of said water-soluble medicines.

* * * * *

UNITED STATES PATENT AND TRADEMARK OFFICE
CERTIFICATE OF CORRECTION

PATENT NO. : 10,898,447 B2
APPLICATION NO. : 16/345448
DATED : January 26, 2021
INVENTOR(S) : Sergey Emilevich Kondakov et al.

Page 1 of 1

It is certified that error appears in the above-identified patent and that said Letters Patent is hereby corrected as shown below:

On the Title Page

(73) Assignee:
Replace Assignee "Psirrros Inc." with --- PSIMOS INC. ---

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*